(12) United States Patent
Burns et al.

(10) Patent No.: US 9,170,205 B2
(45) Date of Patent: Oct. 27, 2015

(54) DISINFECTION AND CLEANING CONFIRMATION SYSTEM

(71) Applicant: Metrex Research, LLC, Orange, CA (US)

(72) Inventors: Steven Joseph Burns, Marina del Rey, CA (US); Abhigyan Som, Brea, CA (US); Walter Joseph Tulpinski, Pomona, CA (US)

(73) Assignee: Metrex Research, LLC, Orange, CA (US)

( * ) Notice: Subject to any disclaimer, the term of this patent is extended or adjusted under 35 U.S.C. 154(b) by 204 days.

(21) Appl. No.: 14/030,940

(22) Filed: Sep. 18, 2013

(65) Prior Publication Data

US 2015/0079690 A1    Mar. 19, 2015

(51) Int. Cl.
  *G01N 21/78* (2006.01)
  *A61L 2/28* (2006.01)

(52) U.S. Cl.
  CPC .. *G01N 21/78* (2013.01); *A61L 2/28* (2013.01)

(58) Field of Classification Search
  CPC ..................................................... G01N 21/78
  USPC ........... 422/430; 436/111–112, 166, 169, 179
  See application file for complete search history.

(56) References Cited

U.S. PATENT DOCUMENTS

| | | | |
|---|---|---|---|
| 2,599,697 A | | 6/1952 | Conklin et al. |
| 2,979,468 A | | 4/1961 | Auerbach et al. |
| 3,317,282 A | | 5/1967 | Antonides et al. |
| 3,899,437 A | * | 8/1975 | Regan et al. .................... 424/52 |
| 3,992,149 A | * | 11/1976 | Wang ............................ 436/164 |
| 4,016,089 A | * | 4/1977 | Regan et al. .................. 510/100 |
| 4,729,834 A | * | 3/1988 | Itoh et al. ....................... 210/670 |
| 6,395,551 B1 | * | 5/2002 | Kipke et al. ........................ 436/1 |
| 7,718,395 B2 | | 5/2010 | Carling |
| 7,780,453 B2 | | 8/2010 | Carling |
| 7,785,109 B2 | | 8/2010 | Carling |
| 8,435,933 B2 | | 5/2013 | Carling |
| 2006/0222675 A1 | * | 10/2006 | Sabnis et al. .................. 424/405 |
| 2007/0138401 A1 | * | 6/2007 | Tokhtuev et al. .............. 250/373 |
| 2008/0264445 A1 | * | 10/2008 | Levitt et al. ........................ 134/6 |
| 2009/0024096 A1 | * | 1/2009 | Hai et al. ....................... 604/265 |
| 2009/0176673 A1 | * | 7/2009 | Hanes ............................ 510/100 |
| 2010/0119561 A1 | * | 5/2010 | Spindler et al. ................ 424/401 |
| 2011/0250626 A1 | * | 10/2011 | Williams et al. ................. 435/18 |
| 2014/0188089 A1 | * | 7/2014 | Midgette et al. .............. 604/539 |

FOREIGN PATENT DOCUMENTS

| | | | |
|---|---|---|---|
| WO | 90/14591 | * | 11/1990 |
| WO | 93/19152 | * | 9/1993 |
| WO | 2007/054238 | * | 5/2007 |

OTHER PUBLICATIONS

Nishida, M. et al, Yukagaku 1976, 25, 21-23.*
Motomizu et al., "Flow-Injection Spectrophotometric Method for the Determination of Anionic Surfactants with an Anionic Azo Dye and a Quaternary Ammonium Ion," Analytical Sciences, Supplement, 7:301-304, 1991.
Motomizu et al., "Spectrophotometric Determination of Cationic and Anionic Surfactants with Anionic Dyes in the Presence of Nonionic Surfactants, Part I: A General Aspect," Mikrochim. Acta, 106:57-66, 1992.
"Guideline for Disinfection and Sterilization in Healthcare Facilities, 2008," U.S. Department of Health and Human Services, Centers for Disease Control and Prevention, Rutala W.A. et al.
"Guidelines for Environmental Infection Control in Health-Care Facilities," U.S. Department of Health and Human Services, Centers for Disease Control and Prevention, (2003).
"Options for Evaluating Environmental Cleaning," U.S. Department of Health and Human Services, Centers for Disease Control and Prevention, Guh, A. et al., 2010.
European Patent Office, European Search Report and Preliminary Opinion issued in corresponding European Patent Application No. 14184985, dated Feb. 19, 2015, 8 pp.

* cited by examiner

*Primary Examiner* — Arlen Soderquist
(74) *Attorney, Agent, or Firm* — Wood, Herron & Evans, LLP

(57) ABSTRACT

An indicator kit for detecting the presence of a quaternary ammonium compound disinfectant is provided. The kit includes an indicator composition that includes an azo dye material and water; an extraction composition that includes water, and at least one of a C1-C7 alcohol or a glycol ether; and an acidic compound present in at least one of the indicator composition, the extraction composition, or an acidic developer solution packaged separately from the indicator composition and the extraction composition. A method of detecting a quaternary ammonium compound disinfectant on a surface is also provided.

20 Claims, No Drawings

DISINFECTION AND CLEANING CONFIRMATION SYSTEM

FIELD OF THE INVENTION

The present invention relates to monitoring disinfection and cleaning of surfaces, and more particularly, to compositions and methods for monitoring the disinfection and cleaning of surfaces in healthcare and institutional environments.

BACKGROUND OF THE INVENTION

During the past decade, controlling and limiting the spread of health care associated pathogens has become one of the more challenging aspects of health care epidemiology. Three pathogens posing significant nosocomial problems are Methicillin Resistant *Staphylococcus Aureus* (MRSA), Vancomycin Resistant *Enterococcus* (VRE), and *Clostridium difficile* (*C. difficile*). Their importance derives from a combination of resistance to presently available treatments and an ability to rapidly spread extensively in the environment around hospitalized patients. MRSA is present in wound infections, as often associated with bed sores and catheters. VRE is present in bowel and urinary tract infections. *C. difficile* is also present in bowel infections and presents as severe diarrhea. For each of these pathogens, control with presently available antibiotics is problematical, if not impossible. Accordingly, a more favorable way to combat the spread of these and other bacteria is through implementation of adequate cleaning and disinfecting procedures. When properly cleaned with a disinfection product, surfaces in close proximity to patients and surfaces that are most likely to be touched by patients and health care workers (e.g., high touch surfaces) do not serve as vectors to transmit infectious disease between patients. In other words, proper cleaning and disinfecting of these surfaces minimizes the risks of infectious outbreaks.

In 2002, the Centers of Disease Control (CDC) recommended that hospitals "thoroughly clean and disinfect environmental medical equipment surfaces on a regular basis". More recently the draft guidelines for disinfection and sterilization in healthcare facilities developed by the CDC emphasize the importance of environmental cleaning and disinfection activities. Although these guidelines specifically state that hospitals should ensure compliance by housekeeping staff with cleaning and disinfecting procedures and ensure consistent cleaning and disinfection of surfaces in close proximity to the patient and likely to be touched by the patient and health care worker (e.g., high touch surfaces), these guidelines provide little in the way of directives regarding the means by which hospitals are to assess their ability to objectively measure the effectiveness of and/or compliance with such cleaning and disinfecting procedures.

Despite the foregoing, environmental hygiene and/or infection control supervisors are increasingly using the currently available cleaning confirmation methods and systems to improve outcomes and meet the increasingly strict regulatory demands. Current cleaning confirmation methods and systems involve direct observation, microbacterial detection (swab cultures or agar slide cultures), detection of markers indicative of microbial metabolism (ATP system), or pre-cleaning application of a transparent material that is subsequently checked for removal. The direct observation method is unduly burdensome on personnel and is highly susceptible to the Hawthorne Effect, which is also commonly referred to as the "observer effect" whereby subjects improve or modify an aspect of their behavior, which is being experimentally measured, in response to the fact that they know that they are being studied. The direct and the indirect microbial detection methods are time intensive and are costly to implement. Concerning the transparent material marker technique, while this technique is less susceptible to the Hawthorne Effect and is less expensive than the microbial detection methods, it requires the additional independent step of applying the transparent marker prior to the cleaning process and a subsequent determination of whether the marker has been washed away during the cleaning process.

Nevertheless, one commercial transparent material marker system currently in use involves the use of a fluorescein gel marker, which is later detected using a black light (i.e., ultraviolet radiation). The fluorescein systems and their use are disclosed in U.S. Pat. Nos. 7,785,109; 7,780,453; 7,718,395, and 8,435,933, for example. However, in addition to the independent application and verification steps, another drawback to the fluorescein systems is that the detection of the fluorescent marker requires the use of a black light.

Despite the aforementioned shortcomings, the current cleaning confirmation methods and systems are still useful tools for educating housekeeping and infection control workers and for monitoring compliance with cleaning protocols. However, none of these current cleaning confirmation systems determine the actual presence (or absence) of any disinfecting agents. In view of the above, there is a need for new cleaning and disinfection confirmation systems that can evaluate the thoroughness with which housekeeping activities are carried out in healthcare settings by detection of disinfecting agents.

SUMMARY OF THE INVENTION

In accordance with an embodiment of the invention, an indicator kit for detecting the presence of a quaternary ammonium compound disinfectant is provided. The indicator kit comprises an indicator composition comprising azo dye material and water; an extraction composition comprising water and at least one of a C1-C7 alcohol or a glycol ether; and an acidic compound present in at least one of the indicator composition, the extraction composition, or an acidic developer solution packaged separately from the indicator composition and the extraction composition.

In accordance with another embodiment of the invention, a method for detecting a presence of a quaternary ammonium compound disinfectant on a surface is provided. The method comprises obtaining a sample from the surface; contacting the sample with an indicator composition comprising an azo dye material, water, and optionally a first acidic compound; and visually observing whether a color change result occurs within the indicator composition thereby indicating the existence or the absence of the quaternary ammonium compound disinfectant on the surface.

The above and other objects and advantages of the present invention shall be made apparent from the following detailed description thereof.

DETAILED DESCRIPTION OF THE INVENTION

Cleaning and disinfecting of patient rooms, operating rooms, dental operatories, procedure suites, common areas and other patient areas, is an ongoing process in healthcare settings, such as in hospitals. Institutionalized settings, such as extended care facilities and prisons, and analogous settings such as cruise ships and barracks, are also settings where effective infection control is of concern. Monitoring of effective disinfection is also of concern in settings such as veterinary care, food processing, hatcheries, abattoirs and similar environments. Each patient occupying a room may be subject to pathogens left by a prior occupant of the room and, in turn, may insert his or her specific pathogens into the room environment. Accordingly, one objective of room cleaning/disinfecting is to decrease the likelihood of the environmental transmission of infection to an occupant of the room. Some room sites are cleaned and disinfected daily while others are cleaned and disinfected following patient occupation. Generally, such housekeeping activities are unsupervised. Correlation of the health of room occupants could provide an indication of the quality of the cleaning and disinfecting, although with significant effort and with significant delay.

As used herein, the term "disinfecting" describes a process that eliminates many or all pathogenic microorganisms.

As used herein, the term "cleaning" describes a process that removes visible or invisible soil (e.g., organic and inorganic material) from objects and surfaces and normally is accomplished manually or mechanically using water with detergents or enzymatic products. Cleaning processes may also include the use of disinfectants, and therefore may include disinfecting the object and surfaces.

All weight percentages are based on the total weight of the specified composition, unless stated otherwise.

Housekeeping surfaces require regular cleaning and removal of soil and dust. Most, if not all, housekeeping surfaces need to be cleaned only with soap and water or a detergent/disinfectant, depending on the nature of the surface and the type and degree of contamination. Cleaning and disinfecting methods and schedules can vary according to the area of the healthcare or institutional facility, type of surface to be cleaned, and the amount and type of soil present. The Environmental Protection Agency (EPA) keeps a registry of approved cleaning and disinfecting formulations that can be used in healthcare settings.

One class of disinfectants commonly used in healthcare and institutional settings is quaternary ammonium compound (QAC) based disinfectants. After a surface of an object has been treated with a solution of the QAC disinfectant, e.g., direct application by spraying or wiping with a substrate wetted with a solution of the QAC disinfectant, a small residue of the QAC disinfectant will remain on the treated surface. Thus, in accordance with an embodiment of the present invention, an indicator kit for detecting the presence of the QAC disinfectant residue on a recently treated surface is provided.

According to embodiments of the present invention, the indicator kit is useful for detecting the presence of quaternary ammonium compounds (QAC) disinfectants. Quaternary ammonium compounds comprise a tetra-substituted nitrogen moiety. According to one embodiment, the QAC disinfectant has a general formula $R_4N^+X^-$, where each R may be the same or different and may be selected from substituted or unsubstituted alkyls, alkenyls, alkaryls, or aryls; and X is a negatively charged counter ion, such as a halide. Exemplary QAC disinfectants include, but are not limited to didecyl dimethyl ammonium chloride (DDAC); N-benzyl-N,N-dimethyl-2-{2-[4-(2,4,4-trimethylpentan-2-yl)phenoxy]ethoxy}ethanaminium chloride, which is commonly known as benzethonium chloride; alkyldimethylethylbenzylammonium choride; and alkyldimethylbenzylammonium chloride.

In accordance with an embodiment of the present invention, the indicator kit comprises an indicator composition comprising azo dye material and water; an extraction composition comprising water and at least one of a C1-C7 alcohol or a glycol ether; and an acidic compound present in at least one of the indicator composition, the extraction composition, or an acidic developer solution packaged separately from the indicator composition and the extraction composition. The azo dye material will undergo a visible color change to indicate the presence of a QAC disinfectant without having to use expensive equipment or time-intensive procedures. Without being bound by any particular theory, it is believed that an azo compound in the azo dye material forms an ion associated complex with the QAC present as a residue on the surface of the object previously treated with the QAC disinfectant, which thereby brings about a color change in the indicator composition. According to an embodiment of the present invention, the indicator composition may further comprise an acidic compound, as described in more detail below.

The indicator composition includes an azo dye material that comprises an azo compound. Exemplary azo compounds include 4-[(4-dimethylamino)phenyl-diazenyl]benzenesulfonic acid, 4-[(4-diethylamino)phenyldiazenyl]benzenesulfonic acid, 4-[(4-dipropylamino)phenyldiazenyl]benzenesulfonic acid, 4-[(4-dibutylamino)phenyl-diazenyl]benzenesulfonic acid, or salts thereof. Common salts, such as alkali metal salts, of the foregoing exemplary azo compounds are also suitable. For example, the sodium salts of the foregoing exemplary azo compounds, which are known by their respective common names methyl orange, ethyl orange, propyl orange, and butyl orange, may be used in the indicator composition. According to an example, the indicator composition includes at least ethyl orange. According to another example, the indicator composition includes a combination of ethyl orange and one or more secondary dyes to provide the indicator composition with a red color that turns green upon reaction with the QAC disinfectant. Exemplary secondary dyes include, but are not limited to, bromothymol blue, Azure A, basic blue, or malachite green, and can be used to adjust the colors of the resultant positive and negative kit indications.

The indicator composition further includes water. The water used in the indicator composition is not particularly limited to any source. For example, suitable sources of water include municipal water, distilled water, or deionized water. In one example, the water is deionized water.

The concentration of the azo dye material, as well as any secondary dyes, in the indicator composition is not particularly limited to any specific range. Moreover, commercial sources of azo dye material can vary in their degree of purity for a specific azo compound. As such, the amount of azo dye material to achieve a given level of coloring to the indicator composition can vary from supplier to supplier and, in some instances, from lot to lot from a single supplier. In one embodiment, the azo compound is present in a sufficient quantity to provide a color change discernible to the testing personnel. In another embodiment, the azo compound is present in the indicator composition at its saturation concentration within the given solution matrix. For example, an azo dye material comprising about 50 wt % ethyl orange may be present in an amount in the range from about 0.01 wt % to about 0.2 wt %; or from about 0.05 wt % to about 0.15 wt %, or from about 0.08 wt % to about 0.12 wt %. In one example, the indicator composition comprises about 0.15 wt % of an azo dye material that comprises about 50 wt % ethyl orange, which would be approximately 2 millimolar ethyl orange (M.W. 355.39 g/mol).

Azo compounds, such as methyl orange, have traditionally been utilized as pH indicators in titrations. As such, one potential false-positive color change could arise if residual materials on the surface being tested were to sufficiently change the pH of the indicator composition. Accordingly, this pH-driven potential side reaction can be suppressed by including a sufficient quantity of an acidic compound in the indicator composition. Thus, in accordance with an embodiment, the indicator composition further includes an acidic compound, such as a carboxylic acid, a phosphoric acid, a sulfonic acid, a mineral acid, or combinations thereof. Exemplary acidic compounds include, but are not limited to, acetic acid, peracetic acid (ethaneperoxoic acid), citric acid, lactic acid, phosphoric acid, hydrochloric acid, 2,4-dodecadienoic acid, caprylic acid, D-gluconic acid, octanoic acid, dodecylbenzenesulfonic acid, para-hydroxybenzoic acid, or combinations thereof. According to an example, the indicator composition includes acetic acid. According to embodiments of the present invention, the acidic compound is present in at least one of the indicator composition, the extraction composition, or an acidic developer solution packaged separately from the indicator composition and the extraction composition.

Thus, according to an embodiment, the acidic compound may be present in the indicator composition in a sufficient quantity to suppress the undesired pH-driven side reaction. For example, the acidic compound can be present in the indicator composition in an amount in the range from about 1 wt % to about 20 wt %, or from about 2 wt % to about 10 wt %, or from about 3 wt % to about 8 wt %. In one example, the indicator composition is a solution comprising about 5 wt % acetic acid.

The indicator composition may further include other additives, such as preservatives or surface tension modifiers. A non-limiting example of a C1-C7 alcohol compound that may serve as both a preservative and a surface tension modifier is ethanol. Additionally, many common surfactant compounds can also serve both functions. In one example, the indicator composition further comprises ethanol.

To facilitate extraction of the QAC disinfectant residue on the testing surface, the indicator kit further includes an extraction composition. In accordance with an embodiment of the present invention, the extraction composition includes water, at least one of a C1-C7 alcohol or a glycol ether, and optionally an acidic compound. For example, the extraction composition may comprise water and the C1-C7 alcohol; or water and the glycol ether; or water, the C1-C7 alcohol, and the glycol ether, of which the acidic compound may be included in any of the foregoing.

However, depending on the time difference between treating the surface with the QAC disinfectant and testing, as well as the type of material making up the surface, the extraction composition can affect the outcome of whether positive or negative results are observed. Exemplary non-porous surfaces commonly found in the medical, institutional, and dental environments include, but are not limited to, polyethylene, polypropylene, stainless steel, laminates, and polyvinylchloride (PVC). Most of the foregoing materials do not significantly absorb and/or ionically bind QACs, and thus, positive color change results are observed using a mildly acidic, e.g., 0.15 wt % acetic acid, extraction composition to obtain a test sample of the surfaces of those materials after more than 24 hours having passed since treating with the QAC disinfectant. However, PVC, which is commonly referred to as "naughahyde" or "pleather", can absorb and/or ionically bind QACs, and has showed a negative color change result 15 minutes after cleaning with a QAC disinfectant when only purified water is used as the extractant. However, it was unexpectedly found that an extraction composition comprising a combination of water, an alcohol, glycol ether, and an acidic compound extended that testing window for the PVC surface by about 16 times or more. Thus, in accordance with another embodiment of the present invention, the extraction composition includes water, a C1-C7 alcohol, a glycol ether, and an acidic compound.

Exemplary C1-C7 alcohols include, but are not limited to, methanol, ethanol, propanol, butanol, pentanol, hexanol, heptanol, ethylene glycol, propane 1,2-diol, propane 1,3-diol, butylene 1,2-glycol, butane 1,4-diol, pentane diols, hexane diols, heptane diols, glycerol, butane triols, pentane triols, hexane triols, or combinations thereof. The various isomers of the foregoing are also envisaged. For example, n-propanol, isopropanol, n-butanol, isobutanol, n-pentanol, isopentanol, n-hexanol, isohexanol, n-heptanol, isoheptanol, and the like are also suitable. According to an example, the extraction composition includes ethanol.

According to an embodiment, the extraction composition comprises the C1-C7 alcohol in an amount in the range from about 1 wt % to about 50 wt %, or from about 5 wt % to about 30 wt %, or from about 10 wt % to about 25 wt %. In one example, the extraction composition comprises about 10 wt % ethanol.

Exemplary glycol ethers include, but are not limited to 2-methoxyethanol, 2-ethoxyethanol, 2-propoxyethanol, 2-isopropoxyethanol, 2-butoxyethanol, 2-phenoxyethanol, 2-benzyloxyethanol, 2-(2-methoxyethoxyl)ethanol, 2-(2-ethoxyethoxyl)ethanol, 2-(2-butoxyethoxyl)ethanol, or combinations thereof. According to an example, the indicator composition includes 2-butoxyethanol. In one example, the extraction composition includes 2-butoxyethanol.

According to an embodiment, the extraction composition comprises the glycol ether in an amount in the range from about 1 wt % to about 50 wt %, or from about 5 wt % to about 30 wt %, or from about 10 wt % to about 25 wt %. In one example, the extraction composition comprises about 20 wt % 2-butoxyethanol.

Exemplary classes of acids and exemplary acidic compounds suitable for use in the extraction composition include, but are not limited to, those described above with respect to the indicator composition. According to an example, the extraction composition includes acetic acid.

According to an embodiment, the extraction composition comprises the acidic compound in an amount in the range from about 0.01 wt % to about 5 wt %, or from about 0.05 wt % to about 2 wt %, or from about 0.1 wt % to about 1 wt %. In one example, the extraction composition comprises about 0.15 wt % acetic acid.

The indicator and extraction compositions may further include common additives, such as surfactants, hydrotropes, preservatives, chelating agents, compatibilizers, etc., which may be present in the respective composition in quantities that do not detrimentally affect the ability of the indicator and extraction compositions to perform their desired function.

An alternative embodiment to incorporating the acidic compound within the indicator composition and/or the extraction composition is to provide the acidic compound as a separately packaged dispensing container. In accordance with this embodiment, the acidic compound may function as an acidic developer solution, which can be added to the indicator composition, the extraction composition, or to a test sample of the extracted surface before or after addition of the indicator composition. In the latter case, a color change induced solely by the pH-driven potential side reaction would be reversed by the subsequent addition of the acidic developer solution.

The indicator composition, the extraction composition, and optionally the acidic developer solution, may be packaged in appropriate dispensing containers, such as a container designed to dispense a predetermined volume. Additionally or alternatively, the acidic compound can be a component of the indicator composition and/or the extraction composition. In any of the foregoing, the acidic compound may be independently selected and may be different in each of the indicator composition, the extraction composition, and/or the acid developer solution. The kit may further include a swabbing device that comprises a support material onto which at least one of the indicator composition or the extraction composition is absorbed.

In one embodiment, a kit is provided containing a plurality of swabbing devices, each pre-wet with the extraction composition and sealed in individual packets. A container of the indicator composition is also provided, for drop-wise dispensing the indicator composition onto the swabbing device after swabbing a test surface with the pre-wet swabbing device. An advantage of the kit of the present invention is the lack of instruments and/or electronically powered devices needed for carrying out the method of disinfection detection.

Suitable swabbing devices for use in embodiments of the invention include, but are not limited to, devices such as test strips, wands, sticks, tubes, chips, channels, wells, cavities, grids, wafers, disks, plates, and cartridges that include the support material. Examples of suitable support materials include, but are not limited to, papers, fibers, fabrics, non-woven fiber mats, felts, porous membranes, porous ceramics, porous hydrophilic plastics, porous sponges, porous polymers, hygroscopic gels, hygroscopic polymers, and porous or hygroscopic natural materials. An example of suitable papers are Whatman™ 3MM available from Whatman, Inc. in Ann Arbor, Mich., which is made from cellulose. Exemplary non-woven fibers include swabs having cotton or cellulose fiber tips. Where test strips are employed, the test strips may be made from a variety of materials and are typically made from one or more pads of paper, which are cut and attached to a polymeric or plastic carrier to form the test strip. Pads for test strips may be made from other woven, nonwoven, patterned, or cast materials including natural and synthetic materials, which are capable of absorbing fluid. Exemplary absorbent materials include polyesters, nitrocelluloses, ceramics, or glass fibers. Accordingly, the indicator composition can be applied to the support material (e.g., paper, pad, etc.) using immersion, spraying, flexographic coating, gravure coating, screen coating, die coating, or a combination of two or more thereof.

Because azo dye compounds can stain many of the non-porous materials commonly found in the medical, institutional, and dental environments, it is not preferred to apply the indicator composition directly onto the surface being tested. Accordingly, in one embodiment, a swabbing device (e.g., 3M™ Enviro Swab, Qosina #19814, or Qosina #66140) is pre-wet with the extraction composition and a portion, e.g., 1.5 in² round testing area, of the surface is swabbed. Afterwards, applying a couple of drops (e.g., 0.03 mL) of the indicator composition to the surface of the swabbing device provides the test sample for observing the color change result. The presence of any QAC disinfectant is indicated by a color change.

Embodiments of the invention, as discussed below, illustrate where monitoring may provide timely assessment as to whether current cleaning and disinfecting activities are consistent with the required procedures. Thus, in accordance with an embodiment of the present invention, a method for determining if a surface has been treated with a quaternary ammonium compound disinfectant is provided, where the method comprises contacting a sample extracted from the surface, and an indicator composition to provide a testing sample; and observing whether a color change occurs within the testing sample thereby indicating the existence or the absence of the quaternary ammonium compound disinfectant. The indicator composition comprises an azo dye material, water, and optionally an acidic compound.

Examples

This invention is illustrated by the following examples that are merely for the purpose of illustration and are not to be regarded as limiting the scope of the invention or the manner in which it can be practiced.

TABLE 1

Exemplary reagents, suppliers, lot numbers, and CAS numbers.

| Description | Supplier | Lot #[a] | CAS number |
|---|---|---|---|
| Acetic Acid (glacial) | J T Baker | K06A12 | 64-19-7 |
| SDA 3C Alcohol (ethyl alcohol) | Archer Daniels Midland | 12816 | 64-17-5 |
| Ethyl Orange, sodium salt | Sigma Aldrich | 16396PHV | 62758-12-7 |
| Bromothymol Blue, sodium salt | Sigma Aldrich | MKBG9478V | 76-59-5 |
| Water (deionized) | Metrex (in house) | Nov. 11, 2012 | 7732-18-5 |
| 2-butoxyethanol | Sasol | 020912 | 111-76-2 |
| Methyl Orange | | | 547-58-0 |
| Propyl Orange | | | 2429-80-3 |
| Butyl Orange | | | 32324-48-4 |

[a]Note:
Lot numbers provided for the reagents used in the indicator and extraction compositions for the testing results shown in Table 2.

Indicator Composition:

An ethyl orange, sodium salt, stock solution was prepared by combining 17.81 g of glacial acetic acid, 51.6 g of SDA-3C ethanol, and 0.59 g of ground ethyl orange, sodium salt in 299.8 g of deionized water and stirred for about 45 minutes, and then further diluted with 161.3 g of deionized water. Stirring was discontinued after 19 hrs, and the mixture was allowed to settle for about an hour, wherein a small quantity of solids settled to the bottom of the container. A liquid portion was decanted from a majority of the solids to provide 510.1 g of the stock ethyl orange solution.

A bromothymol blue stock solution was prepared by combining 4.02 g of glacial acetic acid, 16.11 g of SDA-3C ethanol, and 0.064 g of ground bromothymol blue with 59.94 g of deionized water, and the combination of ingredients was stirred for about 12 hours.

A 3 millimolar (mM) solution of ethyl orange that also contained 0.05 mM bromothymol blue was prepared from the above described stock solutions by combining 482.5 g of the ethyl orange stock solution and 17.70 g of the bromothymol blue stock solution, which was stirred for about an hour. This blend of ethyl orange and bromothymol blue stock solutions provided a red indicator solution that turned green upon mixing with a QAC disinfectant.

Extraction Compositions

Extraction solvent 1 was prepared by diluting 0.15 g of glacial acetic acid to 100 mL with deionized water; extraction solvent 2 was prepared by combining 5 g of SDA-3C ethanol with 45 g of extraction solvent 1; and extraction solvent 5 was prepared by combining 5 g SDA-3C ethanol, and 10 g of 2-butoxyethanol with 35 g of extraction solvent 1. For extraction solvent 3 (100% SDA-3C ethanol) and extraction solvent 4 (100% 2-butoxyethanol), the commercial reagents were used without purification or dilution.

A PVC cloth chair seat was washed with a quaternary ammonium compound disinfectant, CaviWipel™, which is a multi-purpose disinfectant/cleaning wipe available from Metrex Research, LLC, Romulus, Mich. The surface was allowed to air dry at room temperature for 4 hours. After this waiting period, a swab moistened with the extraction composition was used to wipe an area of about 3 in$^2$ of the treated PVC seat surface. Two drops of the indicator composition was applied to the swab and the color change result was noted. If no color change was observed, a negative result was recorded signifying no detection of QAC disinfectant.

As shown in Table 2 below, extraction compositions 1 and 2 failed to provide a positive result after the 4 hour waiting period. However, because the tested area had in fact been disinfected, the failure to indicate a positive color change result is a false negative. Extraction compositions 3 and 4 both provided an observable color change, but a similar result of the placebo control test was obtained, which suggests that the color change result was not indicative of QAC, but due to the extraction composition itself. However, extraction composition 5 provided a clear color change result of red to green after more than 4 hours, while the placebo (pH=12.3) was negative.

TABLE 2

Detection of CaviWipe1 ™ 4 hours after wiping PVC cloth surface.

| | FLUID | Surface Swab Result | Placebo (negative) control result | Comments |
|---|---|---|---|---|
| 1 | 0.15 wt % HOAc[a] | Red (−) | Red (−) | False Negative - indicates PVC has not been cleaned. |
| 2 | 0.15 wt % HOAc, 10 wt % SDA-3C EtOH[b] | Red (−) | Red (−) | False Negative - indicates PVC has not been cleaned. |
| 3 | 100% SDA-3C EtOH | Yellow (+/?) | Yellow (+/?) | Indeterminate result; placebo tends positive, possible false positive |
| 4 | 100% BuOEtOH[c] | Yellow (+/?) | Yellow (+/?) | Indeterminate result; placebo tends positive, possible false positive |
| 5 | 0.15 wt % HOAc, 10 wt % EtOH, 20 wt % BuOEtOH | Green (+) | Red (−) | Functions correctly, QAC treatment detected after 4 hours. |

[a]Acetic acid
[b]Ethanol, 190 proof, denature with isopropanol
[c]BuOEtOH = 2-butoxyethanol or butyl cellosolve Detecting Presence of QAC Disinfectant:

A typical hospital room has a bed section and a lavatory section. The bed section contains common objects such as bed(s), bed rails, bed tray, drape and drape support, telephones, and one or more chairs to provide additional seating. Typical lavatory objects include an entry door, a toilet, a sink, grab bars, and light switches. Doors include knobs or handles for opening and closing. Toilets contain a lid, a seat, and a flush handle. And sinks include faucets, which are generally hand operated. During the course of a hospital stay, a patient is likely to touch many, if not all, of these objects. Accordingly, these types of objects are known in the healthcare settings as high touch objects (HTOs), and may be chosen on the basis of the recommendation from the CDC that enhanced cleaning/disinfecting activities should be directed to these HTOs.

Cleaning personnel should be educated in proper cleaning techniques and may be provided with a checklist of HTOs and surfaces, so as to outline a facility-specific method for controlling nosocomial pathogens. One advantage of the embodiments of the present invention is the ability to spot check whether the cleaning personnel have, in fact, cleaned a given surface, by the direct testing for the presence of residual QAC on the surface. Accordingly, one embodiment of the present invention is basically a method for detecting a presence of a quaternary ammonium compound disinfectant on a surface. The method comprises obtaining a sample from the surface; contacting the sample with an indicator composition comprising an azo dye material; and visually observing whether a color change result occurs within the indicator composition thereby indicating the existence or the absence of the QAC disinfectant on the surface. However, this method alone provides little information toward identifying a time frame of when the QAC was actually applied to the surface.

Accordingly, in another embodiment, a method for determining if a surface has been treated with a quaternary ammonium compound disinfectant is provided, the method comprising obtaining a sample from the surface; contacting the sample with an indicator composition comprising an azo dye material; and visually observing whether a color change result occurs within the indicator composition. In this embodiment, the surface being tested can be pre-cleaned with a material that is void of any quaternary ammonium compound (i.e., a non-quaternary ammonium compound) disinfectant prior to cleaning personnel using a QAC disinfectant to treat the HTOs and prior to obtaining the sample from the surface. As such, any residual QAC disinfectant remaining from the prior QAC treatment is removed. Thus, an absence of a color change result within the indicator composition would indicate that the surface was not treated with the QAC disinfectant during the time period after wiping the surface with the material that is void of any QAC disinfectant to the time of testing. Conversely, a positive color change result would indicate the presence of residual QAC, and that the surface has been cleaned with the QAC. For example, the pre-cleaning may occur between shift changes to enable spot checking of the incoming shift personnel and avoiding QAC residue applied by a previous shift being attributed to the incoming shift.

Non-quaternary ammonium disinfecting materials can include acids, metal ions, oxidants, alcohols, ketones, glycol ethers, aldehydes, biguanides, phenols, iodophors, chelants, or combinations thereof. Table 3 below provides a non-exhaustive listing of exemplary non-quaternary ammonium disinfecting materials.

TABLE 3

Non-quaternary ammonium compound disinfecting actives. Non QAC Active

| General Category | Examples |
|---|---|
| Acids | Citric Acid |
| | Lactic Acid |
| | Phosphoric Acid |
| | Hydrochloric Acid (Hydrogen chloride) |
| | Ethaneperoxoic acid |
| | Ethaneperoxic acid |
| | 2,4-Dodecadienoic acid |
| | Caprylic acid |
| | Peroxyacetic acid |

TABLE 3-continued

Non-quaternary ammonium compound disinfecting actives.
Non QAC Active

| General Category | Examples |
| --- | --- |
|  | D-Gluconic acid |
|  | Acetic Acid |
|  | Octanoic Acid |
|  | Dodecyl-benzenesulfonic acid |
|  | para-Hydroxybenzoic acid |
| Metal Ions | Silver |
|  | Gold |
|  | Copper |
|  | Mercury |
|  | Iron |
| Oxidative Chemistries | Hydrogen Peroxide |
|  | Sodium Chlorite |
|  | Sodium hypochlorite |
|  | Calcium hypochlorite |
|  | Ethylene oxide |
|  | Chlorine dioxide |
| Alcohols | Isopropyl alcohol |
|  | Ethanol |
|  | Methanol |
|  | Butanol |
|  | 2-propanol |
| Biguanide | Polyaminopropyl biguanide (PAPB) |
|  | Polyhexamethylene biguanide (PHMB) |
|  | Polymeric Biguanide Hydrochloride |
|  | Polyhexanide |
| Salts | Sodium Chloride |
|  | Sodium Hydroxides |
| Aldehydes | Glutaraldehyde |
|  | ortho-Phthaladehyde (1,2-benzenedicarboxaldehyde) |
|  | Formaldehyde |
| Phenolics | ortho-Phenylphenol |
|  | ortho-Benzyl-para-Chlorophenol |
|  | Parachlorometaxylenol |
|  | para-tertiary butylphenol |
|  | para-tertiary amylphenol |
|  | Phenol/Phenate |
| Iodophor | Povidone-Iodine |
|  | Polyvinylpyrrolidone with Iodine |
| Chelation | Tetraacetylethylenediamine (N-(hydroxyethyl)-ethylenediaminetriacetic acid) |
| Solvents | Glycol Ethers |
|  | Ketones |
| Other | Tertiary amines |

A complementary approach to the foregoing method is to wipe the surface with a QAC disinfectant as a marker prior to obtaining the sample from the surface to detect whether the surface has been cleaned with a non-QAC disinfectant. In this embodiment, an absence of a color change result within the indicator composition would indicate that the surface was cleaned with a material void of any QAC disinfectant after wiping the surface with the QAC disinfectant. This approach would be useful where an outbreak had been identified and the cleaning protocol in response thereto required cleaning and disinfecting with bleach. In other words, since bleach will remove a QAC, a supervisor could pre-wipe test surfaces on HTOs with the QAC disinfectant and after the cleaning personnel has completed disinfecting the HTOs with bleach, the supervisor can then use the same kit of the present invention to test for the presence of the QAC disinfectant. The kits of the present invention are thus equally useful for both QAC and non-QAC cleaning protocols.

The foregoing methods can be utilized in an overall cleaning personnel training schedule wherein each cleaning personnel (i.e., a worker) is provided with information regarding cleaning techniques, and instructions as to what specific HTOs and surfaces that need to be cleaned. After the cleaning personnel have completed their assigned cleaning tasks, the kit and methods described herein can be applied to spot check their cleaning performance. After the testing is complete, the cleaning personnel can be provided with the color change results and any deficiencies addressed.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and method and illustrative examples shown and described. Accordingly, departures may be made from such details without departing from the scope of the general inventive concept.

What is claimed is:

1. An indicator kit for detecting the presence of a quaternary ammonium compound disinfectant, comprising:
    an indicator composition comprising azo dye material and water;
    an extraction composition comprising water, and at least one of a C1-C7 alcohol or a glycol ether; and
    an acidic compound present in at least one of the indicator composition, the extraction composition, or an acid developer solution packaged separately from the indicator composition and the extraction composition.

2. The kit of claim 1, wherein the azo dye material comprises an azo compound selected from the group consisting of methyl orange, ethyl orange, propyl orange, butyl orange, and combinations thereof.

3. The kit of claim 1, wherein the azo dye material comprises ethyl orange.

4. The kit of claim 1, wherein the extraction composition includes the C1-C7 alcohol selected from methanol, ethanol, propanol, isopropanol, butanol, or combinations thereof.

5. The kit of claim 1, wherein the extraction composition includes the glycol ether selected from 2-methoxyethanol, 2-ethoxyethanol, 2-propoxyethanol, 2-isopropoxyethanol, 2-butoxyethanol, 2-phenoxyethanol, 2-benzyloxyethanol, 2-(2-methoxyethoxyl)ethanol, 2-(2-ethoxyethoxyl)ethanol, 2-(2-butoxyethoxyl)ethanol, or combinations thereof.

6. The kit of claim 5, wherein the glycol ether comprises 2-butoxyethanol.

7. The kit of claim 1, wherein the acidic compound is selected from the group consisting of a carboxylic acid, a phosphoric acid, a sulfonic acid, a mineral acid, and combinations thereof.

8. The kit of claim 1, wherein the extraction composition includes the C1-C7 alcohol and the glycol ether.

9. The kit of claim 1, further comprising:
    a swabbing device comprising a support material, wherein at least one of the indicator composition or the extraction composition are absorbed thereon.

10. The kit of claim 9, wherein the support material comprises papers, fibers, fabrics, non-woven fiber mats, felts, porous membranes, porous ceramics, porous hydrophilic plastics, porous sponges, hygroscopic gels, hygroscopic polymers, porous or hygroscopic natural materials, or a combination thereof.

11. The kit of claim 9, wherein the indicator composition is applied to the support material using immersion, spraying, flexographic coating, gravure coating, screen coating, die coating, or a combination of two or more thereof.

12. A method for detecting a presence of a quaternary ammonium compound disinfectant on a surface, the method comprising:

obtaining a sample from the surface;

contacting the sample with an indicator composition comprising an azo dye material, water, and optionally a first acidic compound; and visually observing whether a color change result occurs within the indicator composition thereby indicating the existence or the absence of the quaternary ammonium compound disinfectant on the surface.

13. The method of claim 12, wherein the azo dye material comprises an azo compound selected from the group consisting of methyl orange, ethyl orange, propyl orange, butyl orange, and combinations thereof.

14. The method of claim 12, wherein obtaining the sample from the surface comprises:

swabbing a portion of the surface with a device comprising a support material, wherein the indicator composition is absorbed on the support material, or wherein an extraction composition comprising water, at least one of a C1-C7 alcohol or a glycol ether, and optionally a second acidic compound, is absorbed on the support material.

15. The method of claim 14, wherein the extraction composition includes the C1-C7 alcohol and the glycol ether.

16. The method of claim 14, wherein the extraction composition is absorbed on the support material.

17. The method of claim 14, wherein contacting the sample with the indicator composition comprises applying a solution of the indicator composition to the device.

18. The method of claim 12, further comprising:

wiping the surface with a material that is void of any quaternary ammonium compound disinfectant prior to obtaining the sample from the surface, wherein an absence of the color change result within the indicator composition indicates that the surface was not treated with the quaternary ammonium compound disinfectant after the wiping the surface with the material that is void of any quaternary ammonium compound disinfectant.

19. The method of claim 18, wherein the material that is void of any quaternary ammonium compound disinfectant comprises an acid, a metal ion, an oxidant, an alcohol, a ketone, a glycol ether, an aldehyde, a biguanide, a phenol, a iodophor, a chelant, or combinations thereof.

20. The method of claim 12, further comprising:

wiping the surface with a quaternary ammonium compound disinfectant prior to obtaining the sample from the surface, wherein an absence of the color change result within the indicator composition indicates that the surface was cleaned with a material void of any quaternary ammonium compound disinfectant after the wiping the surface with the quaternary ammonium compound disinfectant.

* * * * *